United States Patent
Harrison

(10) Patent No.: US 6,254,613 B1
(45) Date of Patent: Jul. 3, 2001

(54) THERMAL COMPRESS FOR APPENDAGE AND METHOD OF TREATING APPENDAGE WITH THERMAL COMPRESS

(76) Inventor: Patricia J. Harrison, 9193 Caleb Dr., Mechanicsville, VA (US) 23116

( * ) Notice: Subject to any disclaimer, the term of this patent is extended or adjusted under 35 U.S.C. 154(b) by 0 days.

(21) Appl. No.: 09/422,325

(22) Filed: Oct. 21, 1999

(51) Int. Cl.[7] .................................................. A61B 17/326
(52) U.S. Cl. .......................... 606/118; 607/108; 607/112
(58) Field of Search ........................... 606/118; 607/111, 607/114, 108, 112; 128/842, 843, 844

(56) References Cited

U.S. PATENT DOCUMENTS

| | | | | |
|---|---|---|---|---|
| 4,356,709 | | 11/1982 | Alexander | 62/530 |
| 4,592,358 | | 6/1986 | Westplate . | |
| 4,678,462 | * | 7/1987 | Vaillancourt | 604/180 |
| 4,756,311 | | 7/1988 | Francis, Jr. . | |
| 4,832,030 | | 5/1989 | De Canto . | |
| 4,844,073 | | 7/1989 | Pohler . | |
| 4,899,749 | * | 2/1990 | Laroso | 607/111 |
| 4,905,998 | * | 3/1990 | Last | 607/108 |
| 4,983,122 | | 1/1991 | Mitnick | 433/229 |
| 5,050,596 | * | 9/1991 | Walasek et al. | 607/11 |
| 5,063,939 | * | 11/1991 | Walston | 607/108 |
| 5,073,169 | * | 12/1991 | Ranken | 604/180 |
| 5,111,810 | | 5/1992 | Fortney . | |
| 5,158,556 | * | 10/1992 | Starley | 128/842 |
| 5,205,298 | * | 4/1993 | Hurst | 128/842 |
| 5,243,974 | | 9/1993 | Allen | 607/108 |
| 5,267,945 | | 12/1993 | Doctor et al. | 602/14 |
| 5,269,788 | | 12/1993 | Nelson, III | 606/118 |
| 5,369,807 | * | 12/1994 | Cho et al. | 607/111 |
| 5,383,921 | * | 1/1995 | Barry | 607/111 |
| 5,584,871 | | 12/1996 | Mosley | 607/108 |
| 5,622,186 | * | 4/1997 | Schwartz | 128/842 |
| 5,697,961 | | 12/1997 | Kiamil | 607/108 |
| 5,716,319 | | 2/1998 | Sembert | 600/38 |
| 5,769,806 | | 6/1998 | Radow | 602/41 |
| 5,823,984 | | 10/1998 | Silverberg | 602/61 |
| 5,839,942 | | 11/1998 | Miller | 450/58 |
| 5,879,315 | * | 3/1999 | Mosley | 607/111 |
| 5,935,091 | | 8/1999 | Friedman | 602/79 |
| 5,935,157 | * | 8/1999 | Harmon | 604/111 |
| 5,989,567 | * | 11/1999 | Dolisi | 606/118 |
| 6,007,836 | * | 12/1999 | Denzer | 128/842 |

\* cited by examiner

*Primary Examiner*—Paul J. Hirsch
(74) *Attorney, Agent, or Firm*—Millen, White, Zelano & Branigan, P.C.

(57) ABSTRACT

An apparatus and method for the therapeutic treatment of an elongated protruding body part. An inner liner and an outer liner, joined together at a proximate end form a cavity there between which is filled with a thermal reservoir material. The inner liner and outer liner are permanently sealed together and shaped to accommodate the body part which is to be thermally treated. The method includes chilling or heating the body part by chilling or heating the apparatus prior to placement over the body part. Preferred embodiments include a sterile inner pocket protected by a removable seal element and self-adhesive straps to secure the device more firmly in place.

2 Claims, 2 Drawing Sheets

THERMAL COMPRESS FOR APPENDAGE AND METHOD OF TREATING APPENDAGE WITH THERMAL COMPRESS

BACKGROUND OF THE INVENTION

1. Field of the Invention

The present invention relates to thermal compresses for body parts, more particularly, to a cold or hot compress that compresses and thermally treats a protruding body part; more particularly to a cold compress for therapeutically reducing pain, swelling, or numbing a protruding body part, and most particularly to a cold compress which numbs an infant's, adolescent's, or adult's penis prior to or after circumcision.

2. Description of the Related Art

Certain religious denominations have a ritual removal of the foreskin of the penis, known as circumcision. Various medical and non-medical opinions believe that circumcision results in better personal hygiene over the lifetime of the male person circumcised.

For whatever reason the operation is undertaken, a large percentage of the worldwide male population undergoes the procedure to remove the foreskin of the penis surgically. Such operation usually occurs early in life, shortly after birth, but it is not unknown for males to have the procedure performed later in life.

Occasionally the procedure may be performed for medically indicated reasons in veterinary applications.

The procedure involves the cutting away of the excess foreskin with a scalpel or other suitable cutting device while holding the foreskin at some distance from the head of the penis. Anesthesia is rarely used on infants, but is more common on older individuals. Lidocaine is sometimes used on infants, however it typically requires injection and has potential adverse side effects.

Additionally, injuries or surgeries to other protruding body parts, such as the finger, could benefit from the application of thermal therapy thereto, with or without compression.

Many different devices and methods for performing circumcisions are known, e.g those disclosed in U.S. Pat. Nos. 5,797,921; 5,746,748; 5,860,988; 5,439,466; 5,163,943; 4,491,136; 3,935,759; 3,892,242; 3,874,389; and 3,566,873; each of which is incorporated herein by reference in its entirety.

Needless to say, many persons regard the penile portion of their anatomy as sensitive, especially to pain, and it is believed and reported anecdotally that there is much pain both during the operation and thereafter.

A few devices are known for the post-operative circumcision care of patients, e.g. those described in U.S. Pat. Nos. 5,935,091 and 5,269,788, which disclosures are incorporated herein by reference. However, none of these are known to address the problem of pain both during the operation and afterwards, and swelling afterwards.

Other means of applying therapeutic thermal treatments to the body are known, e.g. by application to various body parts.

U.S. Pat. No. 4,356,709 describes an ice cap for the head. The ice cap is a bag having an inner and outer wall with an opening for a wearer to insert ice, with an elastic band to retain the bag around the wearer's head.

U.S. Pat. No. 4,592,358 describes a compartmented hot/cold pack with a strap for securing it to a body part.

U.S. Pat. No. 4,832,030 describes a collar apparatus for keeping a hot/cold pack insert about a wearer's neck.

U.S. Pat. No. 4,844,073 describes a device for the treatment of hemorrhoids and rectal tissue which is a one piece tube with a coolant therein, and a sealing cap with a stop to prevent the tube from entering the rectum completely.

U.S. Pat. No. 4,983,122 describes a dental compress with a thermal bag adhered to a mouthpiece for insertion into a wearer's mouth.

U.S. Pat. No. 5,111,810 describes a therapeutic thermal wrap kit with a thermal wrap, a holder, a container, and an insulated bag acting cooperatively to keep a wrap cold or hot for use.

U.S. Pat. No. 5,839,942 describes a post-partum breast engorgement bra which is adjustable and may contain a hold or cold compress.

U.S. Pat. No. 5,243,974 describes an athletic supporter with a pocket adapted to receive a chilling medium to relieve pain in the scrotal or inguinal area.

U.S. Pat. No. 5,716,319 describes a sexual therapeutic device to delay ejaculation by a male containing a pouch for receiving testicles, a cold compress being attached to the pouch to apply coolness to the testicles.

U.S. Pat. No. 5,267,945 describes a finger splint for treating pip joint injuries. The splint includes an elastic sleeve for enclosing a finger, and a gel pack incorporated therein to apply heating or cooling. Straps with velcro are provided to secure the injured finger to an adjacent finger.

A solution to the problem of applying thermal and/or compressive treatment to such body parts is needed.

SUMMARY OF THE INVENTION

An object of the present invention is to provide a cold compress which eases the pain and discomfort of the circumcision itself, and the recovery period thereafter.

It is a further object of the present invention to provide a cold compress which may be utilized in other surgical or non-surgical therapeutic situations.

It is an additional object of the present invention to provide a gentle compression to a wounded or traumatized area of the body while providing heat or cold.

It is an additional object of the present invention to provide a non-toxic, non-invasive local anaesthetic effect on a portion of the body.

It is a further object of the present invention to provide a cold compress for pre-surgical use for infant circumcision.

To achieve these objectives in accordance with the present invention, the cold compress of the present invention provides gentle, size adjusted compression of the penis or similarly shaped body part, e.g. a finger, with a cold or if desired heated effect, thereby relieving the pain and discomfort associated with injury or trauma, beit accidental or surgically induced.

In accordance with the present invention, an inner lining, an outer lining, and an inner fluid are provided in a substantially tubular form. The inner and outer linings are closed at one end, and are sealed together at the other end, with the fluid, paste, or gel disposed therein.

In the preferred embodiment of the present invention, the inner and outer liners are fabricated from a thermoplastic sheet material, with some elasticity thereto. Both liner layers may be resilient and thus may provide compression and envelopment of the penis or offended digit if desired.

In another embodiment, both liners may be sealed again at the distal end and provided with an aperture for allowing fluid to drain, e.g. infant urine or other bodily fluids.

Preferably, the liners are fashioned from an elastic thermoplastic material, e.g. rubber, latex, or other similar material. Other, less elastic materials may be used which are hypo-allergenic to reduce the likelihood of an allergic response.

Preferably, the fluid is a non-toxic slightly to extremely viscous gel with a freezing point below that of water.

Preferably, the device is sterilized and has a removable cover or opening which may be disposed of prior to use.

Other objects, features, and characteristics of the present invention as well as the methods of use of related elements will become more apparent upon consideration of the following description and the appended claims with reference to the accompanying drawings, wherein like reference numbers designate corresponding elements in the various figures.

DETAILED DESCRIPTION OF THE PRESENTLY PREFERRED EMBODIMENT

Figure 1:
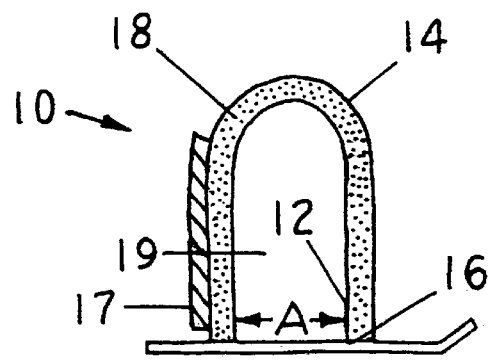
FIG. 1 is a cross sectional view of a preferred embodiment of the present invention.

As shown in FIG. 1, a preferred embodiment of a device according to the instant invention is designated generally by the reference numeral 10. Inner liner 12 is preferably a flexible nonporous sheet material, preferably a thermoplastic material, e.g. polyethylene, polypropylene, polyurethane, or the like. Rubber and latex rubbers may also be suitable for use as an inner liner, although care must be taken to avoid an allergic reaction to latex or the like. Other suitable materials include PVC, silicone, vinyl, and neoprene. Thermosetting polymers may also be used where support is desired of the digit or protuberance.

Suitable materials may be selected from, but are not limited to: ABS plastics, ABS nylon combinations, acetals, acrylic polymers, acrylonitrile, bisphenols, cellulose acetate butyrate, ethylene and polyethylene copolymers, fluoroplastics, furan, low density polyethylene, modified or unmodified polyethylene tetrafluoroethylene, nylon type 6 and 66, PMMA, polyamides, polybutylene terephthalate, polycarbonates, polychlorotrifluoroethylene, polyester (alkyd, thermoplastic, or thermoset), polyethylene terephthalate, polyimide, polystyrene, polystyrene and styrene copolymers, polytetrafluoroethylene, polyvinylidine fluoride, PTFE-filled copolymer, polyvinyl chloride (PVC), PVC-acetate, or polymers and copolymers thereof The inner liner is shaped in a roughly tubular shape narrowing to a sealed tip. The sheet material may be injection molded or formed by other known processes for manufacturing sheet material or as are known in the field of balloon or condom manufacture.

The sheet material may vary widely in thickness, but it is preferred that it be between 0.01–0.50 mm, most preferably about 0.25 mm. Suitable thicknesses may also be between 0.5–3.5 mil, more preferably about 2 mil. A thickness suitable for moldability about an appendage without causing excessive friction is desirable.

The outer liner 14 may be selected from a wide variety of suitable nonporous materials as indicated above for the inner liner. Natural and latex rubbers may be used in fabrication with little fear of allergic response as the exterior of the device does not directly come into contact with the patient's skin if care is taken. Outer liner 14 may also be formed from a rigid or semirigid plastic material.

Both liners may be a single sheet of material or laminates of different material. For example, a pair of laminated films may be used as either liner. One embodiment of the laminate may include an inner film and an outer film formed from any combination of differing materials such as polyethylene, nylon, nylon sclair, polyurethane, or the like. It is preferable if the combination is microwave safe for heat thermal applications.

The outer liner is roughly tubular in shape, but in a preferred embodiment is bulbous, with a slight increase in external diameter at the distal end of the device. This enables more thermal effect, e.g. cooling or heating, to take place at the tip, where most trauma is to be expected in a circumcision.

In a preferred embodiment, the internal diameter tapers to a tip, e.g. for seating the end of the penis or digit securely, comfortable, and in intimate contact with the inner liner of the device to enhance thermal transfer to the underyling skin or tissue.

The two liners are joined together at the proximal end along seal 16. The seal may be formed by welding the two thermoplastic materials together or other such suitable means such as adhesive.

The two liners welded together form a space or void 18 there between. The space is filled with a fluid, liquid, paste, or gel material. Preferably, the liquid, paste or gel has a low freezing point and a high boiling point. One type of gel is constructed according to U.S. Pat. No. 4,756,311, which is incorporated herein in its entirety by reference, as follows: 1350 grams Carbopol™; 13.5 gallons propylene glycol; 180 grams. color dye; 1400 grams formaldehyde; 2000 grams. sodium hydroxide; 37.5 gallons water.

The gel is formed by preparing a dye mix including 22 grams of a food coloring dye added to two quarts of water and a sodium hydroxide mix is prepared including 400 grams of flake sodium hydroxide added to one gallon of water. The dye mix and sodium hydroxide mix are added to an aqueous solution of Carbopol™ including the quantifies as above stated and thereafter propylene glycol and formaldehyde are added. The solution is agitated to achieve a uniform admixture. The propylene glycol is a freezing point depressant and sodium hydroxide functions as a neutralizing agent.

Other suitable gels may also be used, preferably those with a viscosity high enough to maintain a shape when molded into place about a member, e.g a paste-like or almost solid gel consistency at therapeutic temperatures. Gelatinous elastomers, such as those described in U.S. Pat. Nos. 5,633,286; 5,508,334; 5,336,708; and 5,334,646 may be suitable for use. These references are incorporated herein in their entireties by reference.

In a particularly preferred embodiment, an instant cold compress may be contained within the space between the inner and outer layer. A reaction system, e.g. one as described in U.S. Pat. No. 5,123,411, where an endothermic reaction takes place between reactants upon manipulation of the reactants, e.g. by bursting an inner container to cause reactants to come into contact and thereby initiate an endothermic reaction. Instant compresses have long been used to apply cold or heat to human or animal body parts. Materials such as inorganic salts which chill or heat a fluid within the compress may also be used.

A phase change gel material such as that disclosed in U.S. Pat. No. 4,964,402 may also be used herein. Inorganic salt hydrates combined with synthetic polymers to form a thermochemical energy storage material may also be used; such as those disclosed in U.S. Pat No. 4,574,051. Thermal storage materials, as described in U.S. Pat. Nos. 4,273,667 and 4,545,916 also may be suitable for use within the instant invention.

Especially preferred is a phase change gel which becomes more viscous as the temperature drops below 32 degrees F. (0 degrees C.) such that it becomes formable around the digit The skilled artisan may devise any number of suitable gels having regard for this disclosure.

The inner liner delimits a cavity 19, into which an injured or preoperative body protuberance may be inserted to obtain thermal and/or pressure therapeutic effects.

In a preferred embodiment, it may be desirable to include an insulation layer to prevent the cold or heat from affecting other, adjacent body parts (e.g. the scrotum for penile uses, or an adjacent finger for digit uses). In one embodiment the insulation layer may be affixed on the exterior of the outer liner, as illustrated by reference numeral 17.

The two liners sealed together at the proximal end form an aperture (noted at double headed arrow A of FIG. 1) of a certain size, or if round, diameter, which may vary depending on the application of the device.

Figure 2:
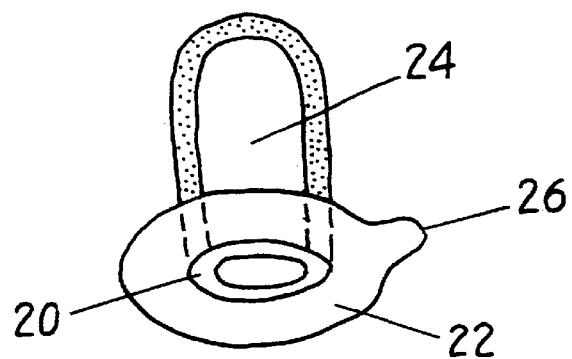
FIG. 2 is a cross-sectional view in partial perspective of a preferred embodiment of the present invention.

Turning now to FIG. 2, a preferred embodiment of the present invention is visible. The seal portion 20 is adhered to closure panel 22, either by way of suitable adhesive or other bond. In this manner the interior cavity 24 is completely sealed from the external environment and may be rendered sterile by any number of known techniques. The closure panel 22 is provided with pull tab 26 for easy grasping and removal of the closure panel and application of the sterile interior to a patient's appendage.

The diameter of the closure panel 22 may vary depending on the application, e.g., circumcision or finger or toe.

Figure three illustrates another embodiment of the invention. The inner and outer liners are joined at the distal end and formed with aperture 30. Aperture 30 allows for the drainage of fluid, e.g. urine, from the penis. Infants especially are unpredictable in their urinary patterns and the sudden infusion of urine onto the epidermis could defeat the cooling purpose of the device. Additionally, if the device is applied postoperatively, urine could act to contaminate the operative site. Therefore, aperture 30 provides a drain.

The device is in this preferred embodiment formed with elastic seal 32, which may be formed from any number of known elastomeric materials. This helps to keep the device mounted on the body protuberance being treated. Suitable elastomerics may include rubber, GR-S (butadiene-styrene copolymer), neoprene, nitrile rubbers, butyl, polysulfide rubbers, ethylene-propylene rubbers, polyurethane rubbers, silicone rubbers, fluorocarbon elastomers, and polyester elastomers.

Figure 3:
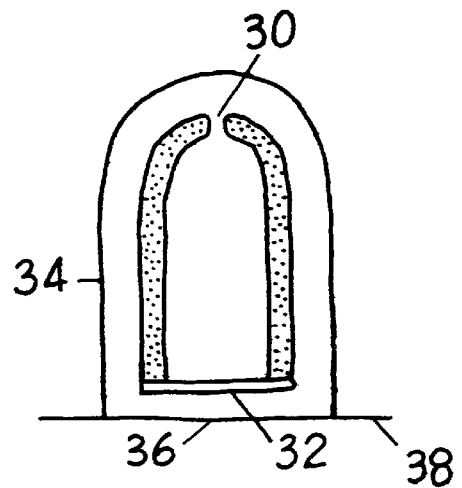
FIG. 3 is a cross sectional view of a preferred embodiment of the present invention.

In the embodiment illustrated in FIG. 3, the device is encased in a sterile container 34 having a seal lid 36 with pull tab 38. This allows the entire device to remain in the sterile condition.

Figure 4:
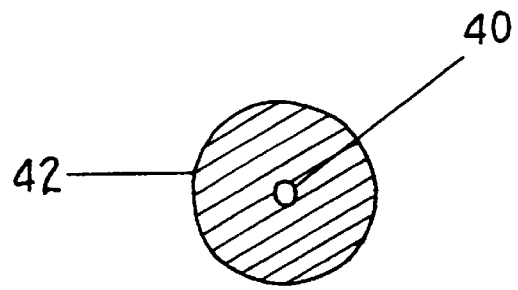
FIG. 4 is a top view of a preferred embodiment of the present invention.

FIG. 4 illustrates the aperture 40 formed in the compress 42.

Figure 5:
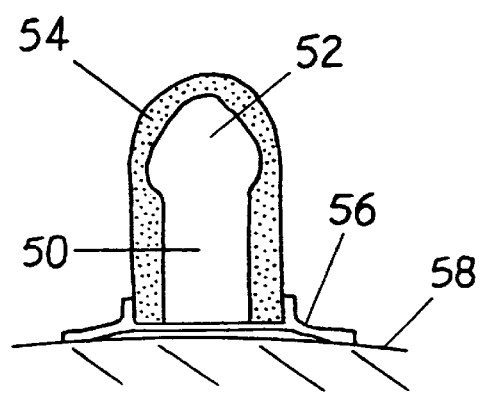
FIG. 5 is a cross sectional view of a preferred embodiment of the present invention in use.

FIG. 5 illustrates the use of the compress in a preoperative patient. The penis 50 and foreskin 52 are inserted into the compress 54. The compress has been preliminarily cooled to a temperature sufficient to cause a numbing effect, preferably between 15–35 degrees F., preferably between 25–32 degrees F. After sufficient time to obtain numbness, for example about 1–5 minutes, preferably about 4–5 minutes, the compress is removed and the operation is performed on a numbed foreskin, thus reducing the pain incurred by the infant or adult in having the circumcision performed.

In another embodiment, lower temperatures may be used for a more immediate numbing effect, e.g. as low as 0–32 degrees F., or lower. Times may then be shortened, if desired, to those which provide the anesthetic effect.

For ease of application and maintenance of the device in place, a pair of attachment straps 56 may be provided. The attachment straps may be self-adhesive or adhere to body surface 58 by any number of known means, tape, hook and loop fasteners, or the like. The strips may be of a wide variety of lengths, but preferably of sufficient length such that the chosen attachment method is sufficient to hold the device in place.

Figure 6:
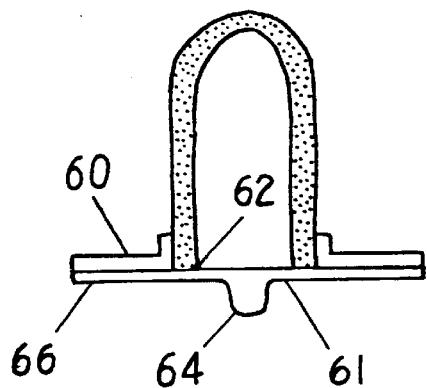
FIG. 6 is a cross sectional view of a preferred embodiment of the present invention.

In a particularly preferred embodiment as illustrated in FIG. 6, the straps 60 are provided with a self adhesive material, and the closure panel 61 is releasably attached at seam 62 to the device. Tab 64 is provided to give purchase for a provider to pull the closure panel from the device, while carrying the backing 66 from the adhesive strip backing, exposing the adhesive while the interior of the device is opened.

After the surgery is completed, a compress according to the present invention may be applied to help reduce bleeding and swelling by applying both pressure and appropriate temperature to the affected region.

By a simple change in the dimensions of the device, it may be rendered suitable for use on, e.g. fingers or the like. Application of cold therapy is a preferred treatment for acute injury. It is especially useful for the preservation of inadvertently amputated body parts, however, it is very difficult to ice a single finger with a conventional prior art ice pack. Maintaining a lower temperature prior to reattachment is critical to tissue survival. On the other hand, application of heat in certain circumstances has been found to act as a vasodilator, to increase tissue metabolism, to increase local circulation, to increase tissue extensibility, and to reduce pain.

Elongated body parts are particularly preferred for this invention, e.g penises, fingers, and toes, parts where the relative length of the part exceeds the width by a significant factor, and an elongated sheath may cover the body part. The ease of use of this device is a great advantage; it may reside in a refrigerator or freezer until it is needed, the sterile packaging be opened, the device be slipped on, is self-retaining, then pulled off and discarded. The device may be manufactured from commonly available low-cost materials.

For example, a low cost thermal reservoir material may be as simple as a saline solution, or a simple carbopol gel made therefrom. No toxic materials are needed for the present invention.

Manufacturing the invention is very simple. The inner and outer liners may be injection molded (similar to infant bottle nipples), filled with the thermal reservoir material, and sealed. Upon appropriate sterilization techniques, e.g. application of heat or chemical disinfectants or other commonly used means, the inner liner, forming the pocket for receiving the body part, may be rendered sterile for keeping an operative field clean.

While the invention has been described in connection with the preferred embodiment, it should be understood readily that the present invention is not limited to the disclosed embodiment. Rather, the present invention is intended to cover various equivalent arrangements and is only limited by the claims which follow.

Having described the invention as above, I claim:

1. An apparatus for applying thermal treatment to an elongated protruding body part, comprising:

an elongated inner liner conforming in shape to the body part to be treated, said inner liner having a proximal end, a distal end and forming a receiving pocket, an elongated outer liner of larger dimensions than said inner liner, said outer liner having a proximal end and a distal end, said inner and outer liners being sealed together at or about the proximal ends to delimit a cavity between said inner and outer liners, said proximal ends forming an aperture for insertion of the body part into said pocket, said cavity containing a thermal reservoir material, said device being configured to envelop the body part in intimate contact, further comprising at least one attachment strap attached thereto, wherein the attachment strap is attached to the outer liner and has a self-adhesive layer, wherein the self-adhesive layer has a backing which is removable; and wherein the backing is attached to a removable seal element removably affixed to the first aperture.

2. A method for the treatment of a penis prior to circumcision, comprising the steps of:

providing an apparatus for applying thermal treatment to an elongated protruding body part, comprising:

an elongated inner liner conforming in shape to the body part to be treated, said inner liner having a proximal end, a distal end and forming a receiving pocket, an elongated outer liner of larger dimensions than said inner liner, said outer liner having a proximal end and a distal end, said inner and outer liners being sealed together at or about the proximal ends to delimit a cavity between said inner and outer liners, said proximal ends forming an aperture for insertion of the body part, into said pocket, said cavity containing a thermal reservoir material, said device being configured to envelop the body part in intimate contact, further comprising a removable seal element removably affixed to the first aperture, and wherein the pocket is sterile, cooling the apparatus to a therapeutically significant temperature prior to circumcision, applying the apparatus to the penis which is to be circumcised, allowing the apparatus to reside upon the penis for a sufficient time so as to impart numbness to the foreskin and surrounding region of the penis, and removing the apparatus from the penis prior to conducting the circumcision upon the penis.

* * * * *